US010143644B2

(12) United States Patent
Gevgilili et al.

(10) Patent No.: US 10,143,644 B2
(45) Date of Patent: Dec. 4, 2018

(54) COMPOSITION COMPRISING AN ANIONIC-AMPHOLYTIC POLYMER ASSOCIATION

(71) Applicant: L'OREAL, Paris (FR)

(72) Inventors: Halil Gevgilili, Weehawken, NJ (US); Catherine Jinhong Kim, Leonia, NJ (US); Marie Huynh, Monmouth Junction, NJ (US); Carmen Castillo-Bucci, Englewood, NJ (US); Aziza Suleiman, Paterson, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/840,866

(22) Filed: Aug. 31, 2015

(65) Prior Publication Data
US 2017/0056315 A1 Mar. 2, 2017

(51) Int. Cl.
| | | |
|---|---|---|
| *A61Q 5/02* | (2006.01) | |
| *A61Q 5/12* | (2006.01) | |
| *A61K 8/81* | (2006.01) | |
| *A61K 8/41* | (2006.01) | |
| *A61K 8/20* | (2006.01) | |
| *A61K 8/37* | (2006.01) | |
| *A61K 8/368* | (2006.01) | |
| *A61K 8/58* | (2006.01) | |
| *A61K 8/34* | (2006.01) | |
| *A61K 8/42* | (2006.01) | |
| *A61K 8/64* | (2006.01) | |
| *A61K 8/46* | (2006.01) | |
| *A61K 8/898* | (2006.01) | |
| *A61K 8/44* | (2006.01) | |

(52) U.S. Cl.
CPC .............. *A61K 8/8152* (2013.01); *A61K 8/20* (2013.01); *A61K 8/342* (2013.01); *A61K 8/345* (2013.01); *A61K 8/368* (2013.01); *A61K 8/37* (2013.01); *A61K 8/41* (2013.01); *A61K 8/416* (2013.01); *A61K 8/42* (2013.01); *A61K 8/44* (2013.01); *A61K 8/463* (2013.01); *A61K 8/585* (2013.01); *A61K 8/645* (2013.01); *A61K 8/8158* (2013.01); *A61K 8/898* (2013.01); *A61Q 5/02* (2013.01); *A61Q 5/12* (2013.01); *A61K 2800/5424* (2013.01); *A61K 2800/5428* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 5,609,862 A | 3/1997 | Chen et al. | |
| 6,028,041 A * | 2/2000 | Decoster | A61K 8/731 |
| | | | 510/119 |
| 8,021,650 B2 | 9/2011 | Tamareselvy et al. | |
| 2013/0284198 A1 | 10/2013 | Rizk et al. | |
| 2015/0150782 A1 | 6/2015 | Johnson | |
| 2015/0283060 A1 * | 10/2015 | Metten | A61Q 5/06 |
| | | | 424/43 |

FOREIGN PATENT DOCUMENTS

WO 2014/071354 A1 5/2014

OTHER PUBLICATIONS

Porter, M.R., "Handbook of Surfactants," published by Blackie & Son (Glasgow and London), 1991, pp. 116-178.
International Search Report and Written Opinion for PCT/US16/49411, dated Nov. 28, 2016.
Lubrizol, "Fixate Design Polymer," 2012, retrieved on Nov. 2, 2016 from internet: [http://www.essentialingredients.com/pdf/FixateDesignBrochure.pdf].
Lubrizol, "Merquat 2003PR Polymer," May 3, 2013, retrieved on Nov. 2, 2016 from internet: [https://www.lubrizol.com/PersonalCare/Products/Merquat/Merquat2003PR.html].
Rohm and Haas, "Acusol Rheology Modifiers," May 2008, retrieved online Nov. 2, 2016 [http://ww.dow.com/assets/attachments/business/acusol_guides/AcusolRheo_low_pdf.

* cited by examiner

*Primary Examiner* — Jyothsna A Venkat
(74) *Attorney, Agent, or Firm* — The Marbury Law Group, PLLC

(57) ABSTRACT

Disclosed are compositions for washing, cleansing, and/or conditioning keratinous substrates, comprising, in a physiologically acceptable medium: a) at least one anionic film-forming polymer chosen from polymers and copolymers of acrylic acid, methacrylic acid, and/or mixtures thereof; b) at least one ampholytic polymer having at least one acrylic acid moiety and a cationic charge density ranging from greater than 1 meq/g up to about 3.5 meq/g; and c) at least one surfactant base; wherein the at least one anionic film-forming polymer and the at least one ampholytic polymer form an association; and wherein the pH of the composition ranges from about 5 to about 7. Also disclosed are processes for washing, cleansing, and/or conditioning keratin substrates using the composition, and processes for imparting volume to the hair.

7 Claims, No Drawings

COMPOSITION COMPRISING AN ANIONIC-AMPHOLYTIC POLYMER ASSOCIATION

FIELD

The present application relates to cosmetic compositions for use on keratinous substrates, such as keratin fibers. In particular, it relates to compositions and methods for washing and/or conditioning hair.

BACKGROUND

The present disclosure relates to personal cleansing and/or conditioning compositions. More particularly, the embodiments of the disclosure relate to rinse-off compositions that provide volumizing properties on keratinous substrates, such as keratin fibers, in particular hair. The disclosure also relates to a hair cleansing and/or conditioning process using this composition.

Certain types of hair are naturally thin and/or fine. In addition, any type of hair can diminish in quality and/or quantity over time by age and/or due to factors such as natural greasiness, sweat, shedded skin cells from the scalp, pollution, and dirt. These factors can result in thinning hair and/or harm the visual appearance and the feel of the hair, and lead to lank body and decreased volume. The magnitude of the consequences of these factors, which are almost all inevitable, is variable, depending on, for example, the quality of the hair, length, style, and environmental factors.

Shampoos are used to combat these drawbacks. Conventional cleansing compositions such as shampoos, for example, contain standard surfactants such as anionic, nonionic and/or amphoteric type surfactants. These compositions can be applied onto a wet keratinous substrate and the lather they generate make it possible, after rinsing with water, to remove the diverse types of soils typically present on the substrate such as hair and/or skin.

These cleansing compositions, while providing good cleansing power, may yield poor intrinsic cosmetic properties due to the fact that the nature of such a cleansing treatment may result in a less conditioned or rough feel to the hair of the hair due to, for example, the gradual removal of the natural or applied fats, lipids, or proteins contained in or at the surface of the hair.

Shampoos sometimes include anionic polymers as thickeners, for example carbomers, carbopols, acrylate-based polymers, and cross-linked polymers. However, none of such anionic polymers typically used in shampoos are anionic film-forming polymers. In addition, shampoos sometimes include cationic polymers such polyquaternium polymers and silicones to provide or enhance cosmeticity effects.

Styling products, for example gels and mousses, are leave-in compositions that may provide volume and body while in the hair. Some leave-in styling products use anionic polymers, for example anionic film-forming polymers, to provide volumizing properties. However, hair tends to be anionic and does not have an affinity for anionic polymers. As such, these polymers can be easily removed from the hair, for example by rinsing or washing. Thus, any cosmetic benefits to the hair from such products are generally diminished or removed once the hair is rinsed or washed.

It is thus an object of embodiments of the disclosure to provide a stable rinse-off cleansing and/or conditioning composition that cleans and/or conditions a keratinous substrate and imparts increased mass, body, and/or volume, while maintaining good deposition and film formation capability on hair fibers to provide excellent volumizing and cosmetic properties, for example long-lasting volume, conditioning, softness, and/or detangling.

According to embodiments of the disclosure, a rinse-off cleansing and/or conditioning composition comprises a surfactant base and an association of at least one anionic film-forming polymer and at least one ampholytic polymer. In at least one exemplary and non-limiting embodiment, the at least one anionic film-forming polymer is chosen from polymers and copolymers of acrylic acid, methacrylic acid, and/or mixtures thereof, and the at least one ampholytic polymer has at least one acrylic acid moiety and a cationic charge density ranging from greater than 1 meq/g to about 3.5 meq/g. It has now been surprisingly and unexpectedly discovered that such a composition is stable and can deliver mass, body, and/or volume to the treated hair. Hair cleansed and/or conditioned with the rinse-off compositions according to embodiments of the disclosure has improved mass, body, and volume.

Also disclosed is a process for washing, cleansing, and/or conditioning the hair and/or the scalp using the composition according to embodiments of the disclosure, the process including applying to the hair a composition as defined above, rinsing off the composition, and optionally drying the hair.

Other subjects, characteristics, aspects and advantages of embodiments of the disclosure will emerge even more clearly on reading the description and the various examples that follow.

BRIEF SUMMARY

Embodiments of the disclosure relate to a composition, for example a rinse-off composition, for cleansing and/or conditioning keratin substrates, the composition comprising:
a. at least one anionic film-forming polymer chosen from polymers and copolymers of acrylic acid, methacrylic acid, and/or mixtures thereof;
b. at least one ampholytic polymer having at least one acrylic acid moiety and a cationic charge density ranging from greater than 1 meq/g to about 3.5 meq/g; and
c. at least one surfactant base;
wherein the at least one anionic film-forming polymer and the at least one ampholytic polymer form an association; and
wherein the pH of the composition ranges from about 5 to about 7.

Embodiments of the disclosure also relate to a process for washing, cleansing, and/or conditioning a keratin substrate, involving applying the above-described composition onto the keratin substrate, and to methods of increasing the volume of the hair by washing, cleansing, and/or conditioning with the above-described composition.

The rinse-off compositions of embodiments of the disclosure may be stable over time and not undergo phase separation.

It is to be understood that both the foregoing general description and the following detailed description are exemplary and explanatory only, and are not restrictive of the disclosure.

DETAILED DESCRIPTION

As used herein, the expression "at least one" means one or more and thus includes individual components as well as mixtures/combinations.

In the present patent application, a species is termed as being "anionic" when it bears at least one permanent negative charge or when it can be ionized as a negatively charged species, under the conditions of use of the compositions of embodiments of the disclosure (for example the medium or the pH) and not comprising any cationic filler.

In the present patent application, a species is termed as being "cationic" when it bears at least one permanent positive charge or when it can be ionized as a positively charged species, under the conditions of use of the compositions of embodiments of the disclosure (for example the medium or the pH) and not comprising any anionic filler.

A species is termed as being "nonionic" when it is neither cationic nor anionic within the meaning of the disclosure, in particular when it comprises no cationic or anionic groups within the meaning of the disclosure.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%), such as within 9%, 8%, 7%, 6%, 5%, 4%, 3%, 2%, or 1%, according to various embodiments.

The term "comprising" (and its grammatical variations) as used herein is used in the inclusive sense of "having" or "including" and not in the exclusive sense of "consisting only of".

"Keratin fiber" as used herein, includes, but is not limited to hair, such as hair on the human head and eyelashes.

As used herein, the terms "applying a composition onto keratin fibers" and "applying a composition onto hair" and variations of these phrases are intended to mean contacting the fibers or hair with at least one of the compositions of the disclosure, in any manner.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The term "stable" as used herein means that the composition does not exhibit phase separation and/or crystallization.

The term "treat" (and its grammatical variations) as used herein refers to the application of the compositions of the present disclosure onto keratin fibers such as hair.

"Volatile", as used herein, means having a flash point of less than about 100° C.

"Non-volatile", as used herein, means having a flash point of greater than about 100° C.

"Substituted" as used herein, means comprising at least one substituent. Non-limiting examples of substituents include atoms, such as oxygen atoms and nitrogen atoms, as well as functional groups, such as acyloxyalky groups, carboxylic acid groups, amine or amino groups, acylamino groups, amide groups, halogen containing groups, ester groups, thiol groups, sulphonate groups, thiosulphate groups, siloxane groups, and polysiloxane groups. The substituent(s) may be further substituted.

The terms "organic compound" and "having an organic structure" mean compounds containing carbon atoms and hydrogen atoms and optionally heteroatoms such as S, O, N or P, alone or in combination.

The term "polymer" is understood to mean, within the meaning of the disclosure, a compound characterized by the multiple repetition of one or more species of atoms or groups of atoms, known as monomers, linked to each other in amounts sufficient to provide a set of properties that do not vary markedly with the addition or removal of one or a few of the monomers.

The term "film-forming polymer" is understood to mean a polymer which is capable of forming, by itself alone or in the presence of an additional film-forming agent, a macroscopically continuous or semi-continuous film on a support, in particular on keratin substances, such as a cohesive film.

The term "rinse-off" is used herein to mean that the hair is rinsed and/or washed either after or during the application of the composition, and before drying and/or styling the hair. At least a portion of the composition is removed from the hair during the rinsing and/or washing. A "leave-on" product refers to a hair care composition that is applied to the hair and not further subjected to a rinsing and/or washing step before drying and/or styling the hair.

The compositions and methods of the present disclosure can comprise, consist of, or consist essentially of the essential elements and limitations of the disclosure described herein, as well as any additional or optional ingredients, components, or limitations described herein or otherwise useful.

In one exemplary and non-limiting embodiment of the present disclosure, the composition, for example the rinse-off composition, for cleansing and/or conditioning keratin substrates comprises:

a. at least one anionic film-forming polymer chosen from polymers and copolymers of acrylic acid, methacrylic acid, and/or mixtures thereof;
b. at least one ampholytic polymer having at least one acrylic acid moiety and a cationic charge density ranging from greater than 1 meq/g to about 3.5 meq/g; and
c. at least one surfactant base;

wherein the at least one anionic film-forming polymer and the at least one ampholytic polymer form an association; and wherein the pH of the composition ranges from about 5 to about 7.

In some embodiments, the cationic charge density of the at least one ampholytic polymer ranges from about 2 meq/g to about 3.1 meq/g.

In other embodiments, the at least one surfactant base comprises at least one surfactant chosen from anionic surfactants.

The compositions according to embodiments of the disclosure may, in various embodiments, have a homogenous texture, i.e., not be lumpy, and may be easy to apply and spread on the hair.

It has been surprisingly and unexpectedly discovered that, in at least certain embodiments, the compositions according to the disclosure may be stable over time, may exhibit no or limited phase separation, and/or may allow retention of the volumizing effect of the association of the at least one anionic film-forming polymer and the at least one ampholytic polymer, such that hair is effectively or satisfactorily volumized after treatment with the composition. It is possible that the volumizing effect imparted to the hair remains even after several washings/cleansings of the hair. In addition, the association of the anionic film-forming polymer and the ampholytic polymer of the compositions of the disclosure may, in various embodiments, result in increased volume and body of the hair.

Anionic Film-Forming Polymer

The at least one anionic film-forming polymer of the disclosure may be chosen from synthetic polymers, natural polymers, modified natural polymers, and mixtures thereof.

In some embodiments, the at least one anionic film-forming polymer is chosen from polymers and copolymers of acrylic acid, methacrylic acid, and/or mixtures thereof.

According to certain embodiments, the at least one anionic film-forming polymer is chosen from polyacrylates, polymethacrylates, and/or mixtures thereof.

In certain embodiments, the anionic film-forming polymer is linear. In other embodiments, the anionic film-forming polymer additionally comprises cross-linking and/or branching.

The at least one anionic film-forming polymer, in certain embodiments, is chosen from silicone acrylate copolymers. In various embodiments, the silicone acrylate copolymer comprises a silicone moiety, a taurate moiety, an acrylic moiety and/or a methacrylic moiety, and/or alkyl ester moieties.

According to other embodiments, the at least one anionic film-forming polymer is a linear copolymer of 2-acrylamido 2-methylpropanesulfonic acid, (meth)acrylic acid and alkyl (meth)acrylate with silicone side chains. In a preferred embodiment, the at least one anionic film-forming polymer is known by its INCI name, Polyacrylate-32, which is commercially available from the company, Lubrizol under the tradename of FIXATE DESIGN POLYMER (31.5% to 34.5% by weight active).

According to various embodiments, the anionic film-forming polymer may have a weight average molecular weight ranging from about 500,000 to about 2,000,000, such as about 700,000 to about 1,5000,000, or about 800,000 to about 1,200,000, or about 800,000 to about 1,000,000, including all ranges and subranges therebetween. In one embodiment, the anionic film-forming polymer has a molecular weight of less than 1,000,000.

The total amount of the anionic film-forming polymer may range from about 0.001% to about 1.0% by weight, based on the total weight of the composition, including all ranges and subranges therebetween.

In certain embodiments, the total amount of the anionic film-forming polymer ranges from about 0.01% to about 0.8% by weight, such as from about 0.05% to about 0.6% by weight, from about 0.1% to about 0.4% by weight, from about 0.15% to about 0.3% by weight, from about 0.18% to about 0.3%, or from about 0.2% to about 0.3%, based on the total weight of the composition, including all ranges and subranges therebetween.

In various embodiments, the total amount of the anionic film-forming polymer is about 0.1%, 0.15%, 0.17%, 0.18%, 0.19%, 0.2%, 0.21%, 0.23, 0.25%, 0.3%, or 0.35% by weight, based on the total weight of the composition.

Ampholytic Polymer

Embodiments of the disclosure employ at least one ampholytic polymer chosen from those that contain units comprising primary, secondary, tertiary and/or quaternary amine groups that may either form part of the main polymer chain or may be borne by a side substituent directly connected thereto.

In certain embodiments, the ampholytic polymer can be pH adjusted to become a cationic polymer.

In certain embodiments, the at least one ampholytic polymer is an ampholytic terpolymer of methacrylamidopropyltrimethylammonium chloride (MAPTAC), acrylamide, and acrylic acid. According to various exemplary and non-limiting embodiments, the ampholytic polymer is an ampholytic terpolymer known by the INCI name of polyquaternium-53 (commercially available from Nalco (Lubrizol), under the tradename, Merquat™ 2003 PR Polymer, 19.5% to 22.5% by weight active).

The at least one ampholytic polymer may optionally be chosen to have chemical properties that are compatible with the at least one anionic film-forming polymer to provide stability to the composition, and/or improve ease of deposition and/or formulation.

In some embodiments, the ampholytic polymer has a monomer distribution such that the overall charge of the ampholytic polymer is moderately to highly cationic. By way of example only, the ampholytic polymer may comprise about 0-20% anionic monomer, about 25-80% cationic monomer, and about 0-70% nonionic monomer. In yet further exemplary embodiments, the ampholytic polymer comprises about 5-15% anionic monomer, about 30-60% cationic monomer, and about 40-60% nonionic monomer.

In certain embodiments, the ampholytic polymer has a ratio of cationic monomer to anionic monomer ranging from greater than about 1 to less than about 5, for example ranging from about 2 to about 1, from about 3 to about 1, from about 4 to about 1, from about 4.5 to about 3.5, or from about 5 to about 3. In certain exemplary embodiments, the ampholytic polymer has a ratio of cationic monomer to anionic monomer ranging from about 4.5 to about 3.5, or from about 5 to about 3.

According to various embodiments, the ampholytic polymer that may be chosen has a cationic charge density optimized to provide desired properties to the composition. Thus, in certain embodiments, the ampholytic polymer has a moderate charge density. Without wishing to be bound by theory, it is believed that in some embodiments, an ampholytic polymer having a moderate charge density can form an association with the anionic film-forming polymer without resulting in an undesirable precipitation or unstable composition. It is further postulated that, in certain embodiments, the ampholytic polymer is attracted to both the anionic polymer and the hair, which has a negative charge. The ampholytic polymer then acts to maintain the anionic polymer on or in close proximity to the hair. According to some embodiments, the ampholytic polymer and anionic polymer are maintained on or in close proximity to the hair even after rinsing and/or washing the hair.

In other embodiments, an ampholytic polymer having a low charge density can lead to a decreased deposition or lack of deposition of the anionic polymer. According to some embodiments, an ampholytic polymer having a charge density less than about 1 meq/g may be too weakly charged to attract the anionic polymer and/or the hair, and/or to maintain the anionic polymer in close proximity to the hair.

According to yet other embodiments, an ampholytic polymer having a very high charge density, i.e., greater than about 3.85 meq/g, may be difficult to stabilize in a composition. The stability issue may be due, for example, to a very strong complexation with the anionic polymer that interferes with the ability of the ampholytic polymer, the anionic polymer, and/or the association between the ampholytic polymer and the anionic polymer to remain in solution and/or suspension within the composition. As a result, this type of very strong complexation can lead to precipitation of the complexed anionic film-forming polymer(s) and ampholytic polymer(s).

In some embodiments, the cationic charge density of the ampholytic polymer ranges from greater than about 1.0 meq/g up to about 3.5 meq/g, such as about 1.8 meq/g to about 3.1 meq/g, about 2.0 meq/g to about 2.8 meq/g, about 2.0 meq/g to about 3.1 meq/g, about 2.4 meq/g to about 3.1 meq/g, or about 2.0 meq/g to about 2.5 meq/g. This charge density may be determined either by calculation from the structure of the polymer or experimentally via the Kjeldahl method. In some embodiments, the charge density of the ampholytic polymer may vary, depending on the pH, which is between about 5 and about 7 in certain embodiments. In some other embodiments, the charge density of the ampholytic polymer is between about 5 and about 6. In one embodiment, when the anionic polymer is Polyacrylate-32, the ampholytic polymer has a cationic charge density of about 2.0 meq/g to about 2.5 meq/g.

In some embodiments, the molecular weight of the ampholytic polymer can affect the volumizing and/or conditioning properties of the composition. In certain embodiments, the volumizing properties of the composition are at least in part determined by film formation, which is in turn at least in part influenced by the molecular weight of the ampholytic polymer.

According to various embodiments, the ampholytic polymer that may be chosen may have a weight average molecular weight ranging from about 500,000 to about 3,000,000, such as about 1,000,000 to about 2,000,000, or about 1,200,000 to about 1,500,000, including all ranges and subranges therebetween. In one embodiment, e.g. when the anionic polymer is Polyacrylate-32, the ampholytic polymer has a molecular weight ranging from about 1,200,000 to about 1,500,000.

The total amount of the ampholytic polymer ranges from about 0.001% to about 1% by weight, based on the total weight of the composition, including all ranges and subranges therebetween.

In certain embodiments, the total amount of the ampholytic polymer ranges from about 0.01% to about 0.8% by weight, such as from about 0.05% to about 0.6% by weight, from about 0.1% to about 0.4% by weight, from about 0.15% to about 0.3% by weight, or from about 0.18% to about 0.3%, by weight, based on the total weight of the composition, including all ranges and subranges therebetween.

In various embodiments, the total amount of the ampholytic polymer is about 0.1%, 0.15%, 0.2%, 0.25%, 0.3%, or 0.35% by weight, based on the total weight of the composition.

Association

In embodiments of the disclosure, the anionic polymer and the ampholytic polymer form an association in the composition. In particular embodiments, the association may result from at least one of electrostatic interactions, hydrogen bonding, Van Der Waals dipole-dipole interactions, steric interactions, hydrophilic interactions, and hydrophobic interactions.

Without being bound by theory, it is believed that the association between the anionic polymer and the ampholytic polymer allows for deposition of the anionic polymer as an anionic film former, and that the ampholytic polymer facilitates deposition of the anionic polymer and also provides balanced cosmeticity to the composition, thereby providing volume to the treated hair.

In some embodiments, the ampholytic polymer is chosen to have at least one monomer in common with the at least one anionic film-forming polymer. In some cases, having a common monomer may result in increase chemical compatibility between the ampholytic polymer and the anionic polymer. The increased chemical compatibility may result in increased attraction between the ampholytic polymer and the anionic polymer. For example, if the anionic polymer is an acrylic film-forming polymer, the ampholytic polymer preferably has at least one acrylate-based monomer.

The weight ratio of the total amount of anionic polymer to the total amount of ampholytic polymer may, according to various non-limiting embodiments, range from about 1:1 to about 1:5, such as from about 1:1 to about 1:3, or from about 1:1 to about 1:2.

Surfactant Base

According to certain embodiments, the composition comprises a surfactant base comprising at least one anionic surfactant, and optionally at least one additional surfactant chosen from anionic surfactants, nonionic surfactants, amphoteric surfactants, and zwitterionic surfactants.

Anionic Surfactant

The term "anionic surfactant" means a surfactant comprising, as ionic or ionizable groups, only anionic groups. A species is termed as being "anionic" when it bears at least one permanent negative charge or when it can be ionized as a negatively charged species, under the conditions of use of the composition (for example the medium or the pH) and not comprising any cationic charge. These anionic groups may be chosen from $-CO_2H$, $-CO_2^-$, $-SO_3H$, $-SO_3^-$, $-OSO_3H$, $-OSO_3^-$, $-H_2PO_3$, $-HPO_3^-$, $-PO_3^{2-}$, $-H_2PO_2$, $=HPO_2$, $-HPO_2^-$, $=PO_2^-$, $=POH$, and $=PO^-$ groups.

The anionic surfactants may be sulfate, sulfonate and/or carboxylic (or carboxylate) surfactants, or mixtures thereof.

Sulfate anionic surfactants comprise at least one sulfate function but do not comprise any carboxylate or sulfonate functions. The sulfate anionic surfactants that may be used comprise at least one sulfate function ($-OSO_3H$ or $-OSO_3^-$).

They may be chosen from the following compounds: alkyl sulfates, alkyl ether sulfates, alkylamido ether sulfates, alkylaryl polyether sulfates, monoglyceride sulfates; and also the salts of these compounds; the alkyl groups of these compounds comprising from 6 to 30 carbon atoms, especially from 12 to 28, better still from 14 to 24 or even from 16 to 22 carbon atoms; the aryl group preferably denoting a phenyl or benzyl group; these compounds possibly being polyoxyalkylenated, especially polyoxyethylenated, and then preferably comprising from 1 to 50 ethylene oxide units and better still from 2 to 10 ethylene oxide units.

Preferentially, the sulfate anionic surfactants are chosen, alone or as a mixture, from:
  alkyl sulfates, especially of C6-C24 or even C12-C20,
  alkyl ether sulfates, especially of C6-C24 or even C12-C20, preferably comprising from 2 to 20 ethylene oxide units;
  in particular in the form of alkali metal or alkaline-earth metal, ammonium or amino alcohol salts.

Sulfonate anionic surfactants comprise at least one sulfonate function ($-SO_3H$ or $-SO_3^-$) and may optionally also comprise one or more sulfate functions, but do not comprise any carboxylate functions. The sulfonate anionic surfactants that may be used comprise at least one sulfonate function ($-SO_3H$ or $-SO_3^-$).

They may be chosen from the following compounds: alkylsulfonates, alkylamidesulfonates, alkylarylsulfonates, α-olefinsulfonates, paraffin sulfonates, alkylsulfosuccinates, alkyl ether sulfosuccinates, alkylamidesulfosuccinates, alkylsulfoacetates, N-acyltaurates, acylisethionates; alkylsulfolaurates; and also the salts of these compounds; the alkyl groups of these compounds comprising from 6 to 30 carbon atoms, especially from 12 to 28, better still from 14 to 24 or even from 16 to 22 carbon atoms; the aryl group preferably denoting a phenyl or benzyl group; these compounds possibly being polyoxyalkylenated, especially polyoxyethylenated, and then preferably comprising from 1 to 50 ethylene oxide units and better still from 2 to 10 ethylene oxide units.

Preferentially, the sulfonate anionic surfactants are chosen, alone or as a mixture, from:
- C6-C24 and especially C12-C20 alkylsulfosuccinates, especially laurylsulfosuccinates;
- C6-C24 and especially C12-C20 alkyl ether sulfosuccinates;
- (C6-C24)acylisethionates and preferably (C12-C18) acylisethionates, in particular in the form of alkali metal or alkaline-earth metal, ammonium or amino alcohol salts.

Carboxylate anionic surfactants comprise at least one carboxylic or carboxylate function (—COOH or —COO$^-$) and may optionally also comprise one or more sulfate and/or sulfonate functions. The carboxylic anionic surfactants that may be used thus comprise at least one carboxylic or carboxylate function (—COOH or —COO$^-$).

They may be chosen from the following compounds: acylglycinates, acyllactylates, acylsarcosinates, acylglutamates; alkyl-D-galactosideuronic acids, alkyl ether carboxylic acids, alkyl(C6-30 aryl) ether carboxylic acids, alkylamido ether carboxylic acids; and also the salts of these compounds; the alkyl and/or acyl groups of these compounds comprising from 6 to 30 carbon atoms, especially from 12 to 28, better still from 14 to 24 or even from 16 to 22 carbon atoms; the aryl group preferably denoting a phenyl or benzyl group; these compounds possibly being polyoxyalkylenated, especially polyoxyethylenated, and then preferably comprising from 1 to 50 ethylene oxide units and better still from 2 to 10 ethylene oxide units.

Use may also be made of the C6-C24 alkyl monoesters of polyglycoside-polycarboxylic acids, such as C6-C24 alkyl polyglycoside-citrates, C6-C24 alkyl polyglycoside-tartrates and C6-C24 alkyl polyglycoside-sulfosuccinates, and salts thereof.

Among the above carboxylic surfactants, mention may be made most particularly of polyoxyalkylenated alkyl(amido) ether carboxylic acids and salts thereof, in particular those comprising from 2 to 50 alkylene oxide and in particular ethylene oxide groups, such as the compounds sold by the company Kao under the name Akypo.

The polyoxyalkylenated alkyl (amido) ether carboxylic acids that may be used are preferably chosen from those of formula (1):

$$R_1\!-\!(OC_2H_4)_n\!-\!OCH_2COOA \qquad (1)$$

wherein:
- R1 represents a linear or branched C6-C24 alkyl or alkenyl radical, an alkyl(C8-C9)phenyl radical, a radical R2CONH—CH2-CH2- with R2 denoting a linear or branched C9-C21 alkyl or alkenyl radical, preferably, R1 is a C8-C20 and preferably C8-C18 alkyl radical, and aryl preferably denotes phenyl,
- n is an integer or decimal number (average value) ranging from 2 to 24 and preferably from 2 to 10,
- A denotes H, ammonium, Na, K, Li, Mg or a monoethanolamine or triethanolamine residue.

It is also possible to use mixtures of compounds of formula (1), in particular mixtures of compounds containing different groups R1.

The polyoxyalkylenated alkyl(amido) ether carboxylic acids that are particularly preferred are those of formula (1) in which:
- R1 denotes a C12-C14 alkyl, cocoyl, oleyl, nonylphenyl or octylphenyl radical,
- A denotes a hydrogen or sodium atom, and
- n varies from 2 to 20 and preferably from 2 to 10.

Even more preferably, use is made of compounds of formula (1) in which R denotes a C12 alkyl radical, A denotes a hydrogen or sodium atom and n ranges from 2 to 10.

Preferentially, the carboxylic anionic surfactants are chosen, alone or as a mixture, from:
- acylglutamates, especially of C6-C24 or even C12-C20, such as stearoylglutamates, and in particular disodium stearoylglutamate;
- acylsarcosinates, especially of C6-C24 or even C12-C20, such as palmitoylsarcosinates, and in particular sodium palmitoylsarcosinate;
- acyllactylates, especially of C12-C28 or even C14-C24, such as behenoyllactylates, and in particular sodium behenoyllactylate;
- C6-C24 and especially C12-C20 acylglycinates;
- (C6-C24)alkyl ether carboxylates and especially (C12-C20)alkyl ether carboxylates;
- polyoxyalkylenated (C$_6$-C$_{24}$)alkyl(amido) ether carboxylic acids, in particular those comprising from 2 to 50 ethylene oxide groups; in particular in the form of alkali metal or alkaline-earth metal, ammonium or amino alcohol salts.

When the anionic surfactant is in salt form, the said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Preferentially, the anionic surfactants are chosen, alone or as a mixture, from:
- C6-C24 and especially C12-C20 alkyl sulfates;
- C6-C24 and especially C12-C20 alkyl ether sulfates; preferably comprising from 2 to 20 ethylene oxide units;
- C6-C24 and especially C12-C20 alkylsulfosuccinates, especially laurylsulfosuccinates;
- C6-C24 and especially C12-C20 alkyl ether sulfosuccinates;
- (C6-C24)acylisethionates and preferably (C12-C18) acylisethionates,
- C6-C24 and especially C12-C20 acylsarcosinates; especially palmitoylsarcosinates;
- (C6-C24)alkyl ether carboxylates, preferably (C12-C20) alkyl ether carboxylates;
- polyoxyalkylenated (C6-C24)alkyl(amido) ether carboxylic acids and salts thereof, in particular those comprising from 2 to 50 alkylene oxide and in particular ethylene oxide groups;
- C6-C24 and especially C12-C20 acylglutamates;
- C6-C24 and especially C12-C20 acylglycinates;

in particular in the form of alkali metal or alkaline-earth metal, ammonium or amino alcohol salts.

In particular, (C$_{12}$-C$_{20}$)alkyl sulfates, (C$_{12}$-C$_{20}$)alkyl ether sulfates comprising from 2 to 20 ethylene oxide units, especially in the form of alkali metal, ammonium, amino alcohol and alkaline-earth metal salts, or a mixture of these compounds, may be chosen. In at least one embodiment, sodium lauryl ether sulfate containing 2.2 mol of ethylene oxide is chosen.

The anionic surfactant is preferably present in the composition in an amount ranging from 0.1% to 30% by weight, especially from 0.5% to 25% by weight and better still from 1% to 20% by weight relative to the total weight of the composition.

Non-Ionic Surfactant

Examples of optional nonionic surfactants that may be used in the composition according to embodiments of the disclosure are described, for example, in the *Handbook of Surfactants* by M. R. Porter, published by Blackie & Son (Glasgow and London), 1991, pp. 116-178. They are especially chosen from alcohols, α-diols and ($C_1$-$C_{20}$)alkylphenols, these compounds being polyethoxylated, polypropoxylated and/or polyglycerolated, the number of ethylene oxide and/or propylene oxide groups possibly ranging from 1 to 100, and the number of glycerol groups possibly ranging from 2 to 30; or alternatively these compounds comprising at least one fatty chain comprising from 8 to 30 carbon atoms and especially from 16 to 30 carbon atoms.

Mention may also be made of condensates of ethylene oxide and of propylene oxide with fatty alcohols; polyethoxylated fatty amides preferably having from 2 to 30 ethylene oxide units, polyglycerolated fatty amides comprising on average from 1 to 5, and in particular from 1.5 to 4, glycerol groups; ethoxylated fatty acid esters of sorbitan preferably containing from 2 to 40 ethylene oxide units, fatty acid esters of sucrose, polyoxyalkylenated and preferably polyoxyethylenated fatty acid esters containing from 2 to 150 mol of ethylene oxide, including oxyethylenated plant oils, N—(C6-24 alkyl)glucamine derivatives, amine oxides such as (C10-14 alkyl)amine oxides or N—(C10-14 acyl) aminopropylmorpholine oxides.

Mention may also be made of nonionic surfactants of alkyl(poly)glycoside type, represented especially by the following general formula:

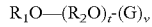

wherein:
$R_1$ represents a linear or branched alkyl or alkenyl radical comprising 6 to 24 carbon atoms and especially 8 to 18 carbon atoms, or an alkylphenyl radical whose linear or branched alkyl radical comprises 6 to 24 carbon atoms and especially 8 to 18 carbon atoms;
$R_2$ represents an alkylene radical comprising 2 to 4 carbon atoms,
G represents a sugar unit comprising 5 to 6 carbon atoms,
t denotes a value ranging from 0 to 10 and preferably 0 to 4,
v denotes a value ranging from 1 to 15 and preferably 1 to 4.

Preferably, the alkylpolyglycoside surfactants are compounds of the formula described above in which:
$R_1$ denotes a linear or branched, saturated or unsaturated alkyl radical comprising from 8 to 18 carbon atoms,
$R_2$ represents an alkylene radical comprising 2 to 4 carbon atoms,
t denotes a value ranging from 0 to 3 and preferably equal to 0,
G denotes glucose, fructose or galactose, preferably glucose;
the degree of polymerization, i.e. the value of v, possibly ranging from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkyl(poly)glycoside surfactant is an alkyl(poly)glucoside surfactant. C8/C16 alkyl(poly)glycosides 1,4, and especially decyl glucosides and caprylyl/capryl glucosides, are most particularly preferred.

Among the commercial products, mention may be made of the products sold by the company COGNIS under the names PLANTAREN® (600 CS/U, 1200 and 2000) or PLANTACARE® (818, 1200 and 2000); the products sold by the company SEPPIC under the names ORAMIX CG 110 and ORAMIX NS 10; the products sold by the company BASF under the name LUTENSOL GD 70, or else the products sold by the company CHEM Y under the name AG10 LK.

Preferably, use is made of C8/C16-alkyl(poly)glycosides 1,4, especially as an aqueous 53% solution, such as those sold by Cognis under the reference Plantacare® 818 UP.

Preferentially, the nonionic surfactants are chosen from (C6-24 alkyl)polyglycosides, and more particularly (C8-18 alkyl)(poly)glycosides, ethoxylated C8-C30 fatty acid esters of sorbitan, polyethoxylated C8-C30 fatty alcohols and polyoxyethylenated C8-C30 fatty acid esters, these compounds preferably containing from 2 to 150 mol of ethylene oxide, and mixtures thereof.

Preferably, when they are present, the composition according to the invention comprises the nonionic surfactant in an amount ranging from 0.01% to 20% by weight, especially ranging from 0.1% to 15% by weight, better still from 0.2% to 10% by weight and preferentially from 0.5% to 5% by weight, relative to the total weight of the composition.

Amphoteric or Zwitterionic Surfactant

The composition according to the invention may optionally also comprise one or more amphoteric surfactants.

The amphoteric surfactants that may be used in the invention may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of (C8-C20)alkylbetaines, sulfobetaines, (C8-C20)alkylsulfobetaines, (C8-C20)alkylamido(C1-C6)alkylbetaines, such as cocamidopropylbetaine, and (C8-C20)alkylamido(C1-C6)alkylsulfobetaines, and mixtures thereof.

Among the optionally quaternized secondary or tertiary aliphatic amine derivatives that may be used, mention may also be made of the products of respective structures (A1) and (A2) below:

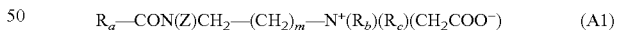

wherein:
$R_a$ represents a $C_{10}$-$C_{30}$ alkyl or alkenyl group derived from an acid $R_a$—COOH preferably present in hydrolysed coconut oil, a heptyl group, a nonyl group or an undecyl group,
$R_b$ represents a β-hydroxyethyl group,
$R_c$ represents a carboxymethyl group;
m is equal to 0, 1 or 2,
Z represents a hydrogen atom or a hydroxyethyl or carboxymethyl group;

wherein:
B represents —$CH_2CH_2OX'$, with X' representing —$CH_2$—COOH, $CH_2$—COOZ', —$CH_2CH_2$—COOH, —$CH_2CH_2$—COOZ', or a hydrogen atom, B' represents —(CH$_2$)$_z$—Y', with z=1 or 2, and Y' representing —COOH, —COOZ', —CH$_2$—CHOH—SO$_3$H or —CH$_2$—CHOH—SO$_3$Z', m' is equal to 0, 1 or 2, Z represents a hydrogen atom or a hydroxyethyl or carboxymethyl group, Z' represents an ion resulting from an alkali or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane, R$_a$' represents a C$_{10}$-C$_{30}$ alkyl or alkenyl group of an acid R$_a$COOH preferably present in hydrolysed linseed oil or coconut oil, an alkyl group, in particular a C$_{17}$ alkyl group, and its iso form, or an unsaturated C$_{17}$ group.

The compounds corresponding to formula (A2) are preferred.

Among the compounds corresponding to formula (A2) in which X' represents an hydrogen atom, mention may be made of compounds classified in the CTFA dictionary, under the names sodium cocoamphoacetate, sodium lauroamphoacetate, sodium caproamphoacetate and sodium capryloamphoacetate.

Other compounds corresponding to formula (A2) are disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium capryloamphodipropionate, lauroamphodipropionic acid and cocoamphodipropionic acid.

Examples that may be mentioned include the cocoamphodiacetate sold by the company Rhodia under the trade name Miranol® C2M Concentrate, the sodium cocoamphoacetate sold under the trade name Miranol Ultra C 32 and the product sold by the company Chimex under the trade name CHIMEXANE HA.

Use may also be made of the compounds of formula (A3):

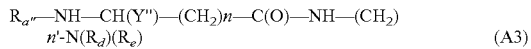

R$_a$"—NH—CH(Y")—(CH$_2$)$n$—C(O)—NH—(CH$_2$)
$n$'-N(R$_d$)(R$_e$)    (A3)

wherein:

R$_a$" represents a C$_{10}$-C$_{30}$ alkyl or alkenyl group of an acid R$_a$"—C(O)OH preferably present in hydrolysed linseed oil or coconut oil;

Y" represents the group —C(O)OH, —C(O)OZ", —CH$_2$—CH(OH)—SO$_3$H or the group —CH$_2$—CH(OH)—SO$_3$—Z", with Z" representing a cationic counterion resulting from an alkali metal or alkaline-earth metal, such as sodium, an ammonium ion or an ion resulting from an organic amine;

R$_d$ and R$_e$ represent, independently of each other, a C1-C4 alkyl or hydroxyalkyl radical; and n and n' denote, independently of each other, an integer ranging from 1 to 3.

Among the compounds corresponding to formula (A3), mention may in particular be made of the compound classified in the CTFA dictionary under the name sodium diethylaminopropyl cocoaspartamide, such as the one sold by the company Chimex under the name CHIMEXANE HB.

Preferably, the amphoteric surfactants are chosen from (C8-C20)alkylbetaines, (C8-C20)alkylamido(C1-C6)alkylbetaines, (C8-C20)alkylamphoacetates and (C8-C20)alkylamphodiacetates, and mixtures thereof.

The total amount of amphoteric and/or zwitterionic surfactant present in the composition is at least about 0.1% by weight, such as from about 0.1% to about 20% by weight, or from about 1% to about 15% by weight, relative to the total weight of the composition.

Water

The compositions according to various embodiments of the disclosure may optionally be aqueous. Water can be present in amounts of about 95% or less, such as about 90%, 80%, 70%, 60%, 50%, 40%, 30%, 20%, 10%, or 5% or less, by weight, based on the total weight of the composition. In further embodiments, water can be present in an amount of about 95%, such as about 90%, 80%, 70%, 60%, 50%, 40%, 30%, 20%, 10%, or 5%, by weight, based on the total weight of the composition, including all ranges and subranges therebetween. Additionally, water can be present in the compositions of the present disclosure in the amount of from about 20% to about 95% by weight, from about 40% to about 90% by weight, or from about 50% to about 80% by weight, based on the total weight of the compositions In other embodiments, water can be present in the compositions of the present disclosure in the amount of at least about 95%, 90%, 80%, 70%, 60%, 50%, 45%, 40%, 30%, 20%, 10%, 5% by weight, based on the total weight of the compositions.

pH

The pH of the compositions according to the disclosure generally ranges from about 5 to about 7, for example from about 5 to about 6.5, or from about 5 to about 6.0, or from about 5 to about 5.5, including ranges and subranges therebetween. In certain embodiments, the pH of the compositions according to the disclosure is about 5.0, such as about 5.1, 5.2, 5.3, 5.4, 5.5, 5.6, 5.7, 5.8, 5.9, or 6.

Additional Components

The composition according to the disclosure may also comprise additives chosen from anionic polymers, nonionic polymers, amphoteric polymers, rheology modifiers, thickening and/or viscosity modifying agents, associative or non-associative polymeric thickeners, non-polymeric thickeners, cationic surfactants, nacreous agents, opacifiers, dyes or pigments, fragrances, mineral, plant or synthetic oils, waxes including ceramides, vitamins, UV-screening agents, free-radical scavengers, antidandruff agents, hair-loss counteractants, hair restorers, preserving agents, pH stabilizers and solvents, and mixtures thereof. A person skilled in the art will take care to select the optional additives and the amount thereof such that they do not harm the properties of the compositions of the present disclosure.

If present in the composition, these additives are generally present in an amount ranging up to about 40% by weight relative to the total weight of the composition, such as up to about 30%, up to about 20%, up to about 15%, up to about 10%, up to about 5%, such as from 0% to 20%.

The compositions of certain embodiments may comprise stabilizers, for example sodium chloride, magnesium dichloride or magnesium sulfate.

The rheology modifiers and thickening/viscosity-modifying agents that may be employed in compositions of the present disclosure may include any water-soluble or water-dispersible compound that is compatible with the compositions of the disclosure, such as acrylic polymers, non-acrylic polymers, starch, cellulose-based polymers, non-polymeric and polymeric gelling agents, silica particles, clay, and mixtures thereof.

The compositions may be packaged in various forms, especially in bottles, in pump bottles or in aerosol containers so as to apply the composition in vaporized form or in the form of a mousse. The compositions may also impregnate applicators, especially gloves or wipes.

The composition may be applied by hand, with an applicator nozzle, with a container equipped with a pump and a dispensing comb, or with an insoluble substrate impregnated with the composition.

Embodiments of the disclosure also relate to a process for washing keratin materials, which consists in applying an effective amount of a composition as defined above to the said keratin materials, and in rinsing, for example with water, after an optional leave-on time.

Certain embodiments also relate to a process for cleansing keratin materials, which consists in applying an effective amount of a composition as defined above to the said keratin materials, and in optionally rinsing, for example with water, after an optional leave-on time.

In some embodiments, treatment with the composition may be followed by application of a conditioning composition, and optionally rinsing the conditioning composition, for example with water, after an optional leave-on time.

As used herein, the method and composition disclosed herein may be used on the hair that has not been artificially dyed, pigmented or permed.

As used herein, the method and composition disclosed herein may be also used on the hair that has been artificially dyed, pigmented or permed.

Processes

The compositions according to the disclosure may be prepared according to techniques that are well known to those skilled in the art.

The compositions may be applied to keratinous substrates, such as the hair, and subsequently rinsed off. In various embodiments, the compositions comprise shampoo compositions for shampooing and/or conditioning the hair, and in various embodiments the shampoo composition will traditionally be rinsed off the hair within a short period of time after application to the hair, such as a period of time up to about 10 minutes, up to about 5 minutes, or up to about 2 minutes after application to the hair.

In various embodiments, processes according to the disclosure comprise applying the compositions described to keratinous substrates, such as the hair, and subsequently rinsing the compositions off. The processes may, in various embodiments, impart volume to the keratinous substrate to which the composition is applied, even after the composition is rinsed off.

Although the foregoing refers to various exemplary embodiments, it will be understood that the disclosure is not so limited. It will occur to those of ordinary skill in the art that various modifications may be made to the disclosed embodiments and that such modifications are intended to be within the scope of the disclosure. Where an embodiment employing a particular structure and/or configuration is illustrated in the present disclosure, it is understood that the present disclosure may be practiced with any other compatible structures and/or configurations that are functionally equivalent provided that such substitutions are not explicitly forbidden or otherwise known to be impossible to one of ordinary skill in the art.

It is also to be understood that, as used herein the terms "the," "a," or "an," mean "at least one," and should not be limited to "only one" unless explicitly indicated to the contrary. Thus, for example, reference to "a layer" includes examples having two or more layers unless the context clearly indicates otherwise.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. For example, the phrase "from about A to C, such as B," is intended to convey at least the following: "about A to about C," "exactly A to exactly C," "about A to exactly C," "exactly A to about C," "about A to about B," "exactly A to exactly B," "about A to exactly B," "exactly A to about B," "about B to about C," "exactly B to exactly C," "about B to exactly C," "exactly B to about C," "about A," "exactly A," "about B," "exactly B," "about C," and "exactly C."

The terms "substantial," "substantially," "about", and variations thereof as used herein are intended to note that a described feature is equal or approximately equal to a value or description.

Unless otherwise expressly stated, it is in no way intended that any method set forth herein be construed as requiring that its steps be performed in a specific order. Accordingly, where a method does not actually recite an order to be followed by its steps or it is not otherwise specifically stated in the claims or descriptions that the steps are to be limited to a specific order, it is not intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method that comprises A+B+C include embodiments where a method consists of A+B+C and embodiments where a method consists essentially of A+B+C.

It will be apparent to those skilled in the art that various modifications and variations can be made to the present disclosure without departing from the spirit and scope of the disclosure. Since modifications combinations, sub-combinations and variations of the disclosed embodiments incorporating the spirit and substance of the disclosure may occur to persons skilled in the art, the disclosure should be construed to include everything within the scope of the appended claims and their equivalents.

EXAMPLES

The following Examples are intended to be non-restrictive and explanatory only, with the scope of the disclosure being defined by the claims.

The ingredient amounts in the compositions/formulas described below are expressed in % by weight, based on the total weight of the composition/formula.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective measurements. The following examples are intended to illustrate the disclosure without limiting the scope as a result.

Example 1: Shampoo Comparison

TABLE 1
Shampoo Compositions

| INCI US | Formula A % by weight | Comparative Formula B (volumizing shampoo) % by weight |
|---|---|---|
| SODIUM HYDROXIDE AMINOMETHYL PROPANOL | — | 0.018 |
| ARGININE | 0.06 | 0.06 |
| SERINE | 0.03 | 0.03 |
| GLUTAMIC ACID | 0.06 | 0.06 |
| SODIUM CHLORIDE | 1.185 | 1.185 |
| TRIETHANOLAMINE | 0.084 | — |
| CITRIC ACID SOLUBLE COLLAGEN | | 0.1 |
| GLYCOL DISTEARATE | 1 | 1 |
| FRAGRANCE | 1 | 1 |
| CARBOMER[a] (98% by weight active) | 0.3 | 0.3 |
| POLYQUATERNIUM-16[b] (40% by weight active) | — | 0.2 |
| POLYQUATERNIUM-53[c] (20.54% by weight active) | 1 | — |
| POLYACRYLATE-32[d] (33% by weight active) | 0.6 | |
| SALICYLIC ACID | 0.5 | 0.5 |
| SODIUM BENZOATE | 0.5 | 0.5 |
| DIMETHICONE | | 0.3975 |
| POLYSILICONE-8[e] (97% by weight active) | | 0.2 |
| AMINOPROPYL TRIETHOXYSILANE | 0.01 | 0.01 |
| HEXYLENE GLYCOL | 0.6 | 0.6 |
| WATER | 60.496 | 61.21574 |
| GLYCERIN | 2 | 2 |
| COCAMIDE MEA | | 2.25 |
| HYDROXYPROPYLTRIMONIUM HYDROLYZED WHEAT PROTEIN | 0.1 | 0.1 |
| COCAMIDE MIPA | 2.25 | |
| SODIUM LAURETH SULFATE[f] (70% by weight active) | 15.625 | 15.67376 |
| SODIUM LAURYL SULFATE[g] (29% by weight active) | 13.8 | 13.8 |

[a] known by the tradename CARBOPOL 980, supplied by Lubrizol or ACRYPOL 980, supplied by Corel Pharma Chem, or ASHLAND 980 MS CARBOMER, supplied by Ashland
[b] known by the tradename LUVIQUAT EXCELLENCE, supplied by BASF, molecular weight of 40,000 and cationic charge density of 6.1 meq/g
[c] known by the tradename MERQUAT 2003PR POLYMER, supplied by Nalco-Lubrizol
[d] known by the tradename FIXATE DESIGN, supplied by Nalco-Lubrizol
[e] known by the tradename L021 DRY, supplied by 3M
[f,g] available from many suppliers Shampoo Formula A was prepared according to Table 1 and the following protocol.

Protocol

Preparation of Annex

18% by weight of the total water used was mixed with Triethanolamine into a container. The batch was then heated to 70-75° C.

Polyacrylate-32 was slowly added to the mixture and was stirred until the batch turned completely clear.

Cocamide MIPA was added and mixed until it dissolved completely.

The batch was maintained at 70-75° C.

Preparation of Main Kettle

The remaining water was added to the kettle and carbomer was sprinkled in slowly.

Once the mixture was completely hydrated, sodium laureth sulfate was added and mixed well.

Sodium lauryl sulfate was added and mixed well.

Polyquaternium-53 was added and mixed well.

Sodium benzoate, salicylic acid, glycerin, and sodium chloride were all added to the batch and mixed well.

A mixture of sodium laureth sulfate, glycol distearate, sodium chloride, and water was added and mixed.

The contents of the Annex phase was added and mixed.

Arginine, serine, glutamic acid, aminopropyl triethoxysilane, hydroxypropyl trimonium hydrolyzed wheat protein, and fragrance were added and mixed well.

Sodium hydroxide or citric acid was added to the resulting final composition.

The stability of the resulting composition was measured at 4, 25, 37 and 45 C up to 8 weeks, no phase separation and the pH remained from between 5 to 5.6, specific gravity >=1.02.

Comparative Formula B was prepared according to Table 1.

Formula A and Comparative Formula B were tested on the hair of the heads of 12 human panelists in a salon. Panelists consisted of women with very fine to fine hair diameter, lightly sensitized, and medium to long hair length. Both formulas were applied and evaluated on the same person, with Formula A applied to half of the head, and Comparative Formula B applied to the other half of the head for each human panelist.

Formula A performed statistically significantly better than Comparative Formula B with respect to abundance of foam, foam stability, ease of shaping with a brush, and volume.

Example 2: Shampoo and Conditioner Comparison

TABLE 2
Conditioner Formula C

| INCI US | Formula C % by weight |
|---|---|
| TARTARIC ACID | 0.14 |
| CETEARYL ALCOHOL | 3.26 |
| CETYL ESTERS (and) CETYL ESTERS | 0.78 |
| FRAGRANCE | 0.7 |
| PHENOXYETHANOL | 0.7 |
| AMODIMETHICONE (and) TRIDECETH-6 (and) CETRIMONIUM CHLORIDE | 0.4 |
| WATER | 92.52 |
| STEARAMIDOPROPYL DIMETHYLAMINE | 1.5 |

TABLE 3
Conditioner Formula D

| INCI US | Formula D (conditioner composition) % by weight |
|---|---|
| ARGININE | 0.06 |
| SERINE | 0.03 |
| GLUTAMIC ACID | 0.06 |
| CITRIC ACID | 0.017 |
| SOLUBLE COLLAGEN | 0.1 |
| CETEARYL ALCOHOL | 1 |
| FRAGRANCE | 1 |
| CHLORHEXIDINE DIHYDROCHLORIDE | 0.03 |
| PHENOXYETHANOL | 0.7 |
| AMODIMETHICONE (and) TRIDECETH-6 (and) CETRIMONIUM CHLORIDE | 1.5 |
| AMINOPROPYL TRIETHOXYSILANE | 0.01 |
| WATER | 89.393 |
| GLYCERIN | 1 |
| BEHENTRIMONIUM CHLORIDE | 1 |
| HYDROXYPROPYLTRIMONIUM HYDROLYZED WHEAT PROTEIN | 0.1 |

TABLE 3-continued

Conditioner Formula D

| INCI US | Formula D (conditioner composition) % by weight |
|---|---|
| CETEARYL ALCOHOL (and) BEHENTRIMONIUM METHOSULFATE | 4 |

Conditioners Formula C and Formula D were prepared according to Table 2 and Table 3. Shampoo Formula A and Conditioner Formula D, and Shampoo Comparative Formula B and Conditioner Formula D were tested in a consumer flash test of 18 human panelists at home. Panelists consisted of Caucasian women ages 18-60, with self-perceived fine hair, medium to long hair length, and who typically washed their hair everyday using commercial shampoo/conditioner bundles. The panelists were asked to use each of the inventive bundle, Shampoo Formula A and Conditioner Formula C, and comparative bundle, Shampoo Comparative Formula B and Conditioner Formula D, at least 3 times, with a 2 day wash-out period between bundles, and asked to answer closed-ended questionnaire.

The combination of Shampoo Formula A followed by Conditioner Formula C performed statistically significantly better than the combination of Comparative Shampoo Formula B followed by Conditioner Formula D with respect to volume and body, no observable build-up of product, and not being heavy on the hair. In addition, the combination of Shampoo Formula A followed by Conditioner Formula D performed comparably to the combination of Comparative Shampoo Formula B followed by Conditioner Formula D with respect to movement, usage qualities, easy styling, clean feel, smoothness, suppleness, softness, and frizz control.

Example 3: Shampoo and Conditioner Comparison

TABLE 4

Comparative Commercial Shampoo Formula E
(advertised for its volumizing properties)
INCI US WATER
SODIUM LAURYL SULFATE
SODIUM LAURETH SULFATE
COCAMIDOPROPYL BETAINE
SODIUM CITRATE
SODIUM XYLENESULFONATE
FRAGRANCE
SODIUM CHLORIDE
CITRIC ACID
SODIUM BENZOATE
HYDROXYPROPYL METHYLCELLULOSE
TETRASODIUM EDTA
TRISODIUM ETHYLENEDIAMINE DISUCCINATE
PANTHENOL
PANTHENYL ETHYL ETHER
METHYLCHLOROISOTHIAZOLINONE
METHYLISOTHIAZOLINONE

TABLE 5

Comparative Commercial Conditioner Formula F
(advertised for its volumizing properties)
INCI US WATER
CETYL ALCOHOL (C16)
STEARAMIDOPROPYL DIMETHYLAMINE
STEARYL ALCOHOL (C18)
QUATERNIUM 18 (di(hydrogenated tallow)-dimethylammonium)
FRAGRANCE
BIS AMINOPROPYL DIMETHICONE
BENZYL ALCOHOL (preservative)
CETARYL ALCOHOL
HYDROXYPROPYL GUAR (slip and viscosity)
GLYCERYL STEARATE (double fatty chain ester)
CITRIC ACID
POLYSORBATE 60 (non ionic surfactant, emulsifier)
EDTA (chelator)
PANTHENOL (humectants, emollient)
PANTHENYL ETHYL ETHER
OLEYL ALCHOL
TRISODIUM ETHYLENEDIAMINE DISUCCINATE (chelating)
METHYLCHLOROISOTHIAZOLINONE
METHYLISOTHIAZOLINONE (preservative)

An embodiment of the disclosure was compared with a commercial product using a shampoo-conditioner regimen. Shampoo Formula A prepared according to Table 1, and Conditioner Formula C prepared according to Table 2 were compared to Comparative Commercial Shampoo Formula E having the ingredients listed in Table 4, and Comparative Commercial Conditioner Formula F having the ingredients listed in Table 5.

The shampoos-conditioners were tested on the hair of the heads of 12 human panelists in a salon. Panelists consisted of women with very fine to fine hair diameter, lightly sensitized, and medium to long hair length. Both formula pairs were applied and evaluated on the same person, with Shampoo Formula A followed by Conditioner Formula C applied to half of the head, and Comparative Commercial Shampoo Formula E followed by Comparative Commercial Conditioner Formula F applied to the other half of the head for each human panelist.

Shampoo Formula A followed by Conditioner Formula C performed statistically significantly better than Comparative Commercial Shampoo Formula E followed by Comparative Commercial Conditioner Formula F with respect to hair smoothness, suppleness with rinsing, detangling, smooth hair feel after rinsing, ease of passing fingers thorough hair, wet suppleness, ease of blow dry, ease of shaping with a brush, discipline, providing shape, smooth hair feel, feel of the product coating the hair after blow drying and hair fibers not clumping together (individualized fibers).

It is to be understood that the foregoing describes preferred embodiments of the disclosure and that modifications may be made therein without departing from the spirit or scope of the disclosure as set forth in the claims.

What is claimed is:
1. A rinse-off composition for cleansing hair, the composition comprising:
    Polyacrylate-32 in an amount ranging from about 0.1% to about 0.4% by weight, based on the total weight of the composition;
    Polyquaternium-53 in an amount ranging from about 0.1% to about 0.4% by weight, based on the total weight of the composition; and at least one anionic surfactant in an amount ranging from about 0.1% to about 30% by weight, based on the total weight of the composition;

wherein the pH of the composition ranges from about 5 to about 7.

2. The composition according to claim 1, wherein the total amount of the Polyacrylate-32 ranges from about 0.15% to about 0.35% by weight of active material, based on the total weight of the composition.

3. The composition according to claim 1, wherein the total amount of the Polyquaternium-53 ranges from about 0.15% to about 0.35% by weight of active material, based on the total weight of the composition.

4. The composition according to claim 1, wherein the weight ratio of the Polyacrylate-32 to the Polyquaternium-53 ranges from about 1:1 to about 1:2.

5. A method for cleansing hair, the method comprising:
contacting the hair with a rinse-off composition comprising:

Polyacrylate-32 in an amount ranging from about 0.1% to about 0.4% by weight, based on the total weight of the composition;

Polyquaternium-53 in an amount ranging from about 0.1% to about 0.4% by weight, based on the total weight of the composition; and at least one anionic surfactant in an amount ranging from about 0.1% to about 30% by weight, based on the total weight of the composition, wherein the pH of the composition ranges from about 5 to about 7.

6. The method according to claim 5, further comprising leaving the composition on the hair for a leave-on time prior to rinsing the hair with water.

7. The method according to claim 6, further comprising drying the hair.

* * * * *